United States Patent
Magarvey

(10) Patent No.: US 7,608,448 B2
(45) Date of Patent: Oct. 27, 2009

(54) METHOD AND CLONING VECTORS UTILIZING INTERGENERIC CONJUGATION FOR MANIPULATION OF ACTINOMYCETES BIOSYNTHESIS GENES

(75) Inventor: Nathan Magarvey, Minneapolis, MN (US)

(73) Assignee: Wyeth, Madison, NJ (US)

( * ) Notice: Subject to any disclaimer, the term of this patent is extended or adjusted under 35 U.S.C. 154(b) by 125 days.

(21) Appl. No.: 10/402,841

(22) Filed: Mar. 28, 2003

(65) Prior Publication Data

US 2003/0224484 A1 Dec. 4, 2003

Related U.S. Application Data

(60) Provisional application No. 60/368,712, filed on Mar. 29, 2002.

(51) Int. Cl.
*C12N 15/09* (2006.01)
*C12N 15/70* (2006.01)
*C12N 15/76* (2006.01)
*C12N 15/74* (2006.01)

(52) U.S. Cl. ............... 435/320.1; 435/69.1; 435/252.3; 435/252.33; 435/252.4

(58) Field of Classification Search ............... 435/320.1, 435/69.1, 252.3, 252.33, 252.34; 536/23.1, 536/24.1, 24.2
See application file for complete search history.

(56) References Cited

U.S. PATENT DOCUMENTS

| | | | | |
|---|---|---|---|---|
| 4,624,926 A | * | 11/1986 | Inouye et al. | 435/252.33 |
| 5,908,764 A | | 6/1999 | Bunker et al. | 435/76 |
| 5,977,439 A | * | 11/1999 | Hamilton | 800/294 |
| 6,242,211 B1 | * | 6/2001 | Peterson et al. | 435/41 |
| 2002/0015989 A1 | | 2/2002 | Hosted, Jr. et al. | |

FOREIGN PATENT DOCUMENTS

| EP | 0 620 280 A1 | | 10/1994 |
|---|---|---|---|
| WO | WO 99/00517 | * | 1/1999 |

OTHER PUBLICATIONS

Bailey et al, Properties of in vitro recombinant derivatives of pJV1, a multicopy plasmid from Streptomyces phaeochromogenes, J Gen Microbiol, 1986, 132(8), pp. 2071-2078.*
Baltz et al., Molecular genetic methods for improving secondary metabolite production in Actinomyctes. Trends Biotechnol. 1996; 14: 245-50.
Flett et al., High efficiency intergeneric conjugal transfer of plasmid DNA from *Escherchia coli* to methyl DNA-restricting streptomycetes. FEMS Micorbiol. Lett. 1997; 155: 223-9.
Mazodier et al., Intergeneric conjugation between *Escherichia coli* and Streptomyces species. J. Bacteriol. 1989; 171: 3583-85.

* cited by examiner

*Primary Examiner*—Maria B Marvich
(74) *Attorney, Agent, or Firm*—Darby & Darby P.C.

(57) ABSTRACT

The present invention relates to a vector comprising sequences that permit direct transfer of the vector from one prokaryotic cell to another, such as by intergeneric conjugation. The invention also relates to methods of making and using the vector.

18 Claims, 8 Drawing Sheets

METHOD AND CLONING VECTORS UTILIZING INTERGENERIC CONJUGATION FOR MANIPULATION OF ACTINOMYCETES BIOSYNTHESIS GENES

This application claims priority from U.S. Provisional Patent Application Ser. No. 60/368,712, filed Mar. 29, 2002, which is herein incorporated by reference in its entirety.

FIELD OF THE INVENTION

The present invention relates to modification of bacterial genes. In particular, the invention relates to vectors and methods for directed homologous recombination of bacterial genes.

BACKGROUND OF THE INVENTION

Bioactive molecules that are isolated from plants, bacteria, and fungi are often referred to as natural products. These molecules are synthesized by primary or secondary pathways within the organism or may even be degradation products of another molecule. However, many of these molecules have shown a variety of therapeutic uses in humans and other animal species. One of the best known examples is taxol, which was originally isolated from the bark of the Pacific Yew tree. Taxol has been shown to have anti-cancer properties and is currently used in the treatment of breast cancer.

Actinomycetes are prolific producers of bioactive small molecules, which may have a variety of clinical applications such as immunosuppressants, antibiotics, and cancer therapeutics. Actinomycetes are Gram-positive bacteria that form long, thread-like branched filaments. The term actinomycetes is used to indicate organisms belonging to the Actinomycetales, an Order of the domain Bacteria. The Actinomycetales are divided into 34 Families including Streptomyceteae, to which belongs the genus *Streptomyces* (Bergy's Manual of Systematic Bacteriology, Second Edition, 2001; George M. Garrity, Editor-in-Chief, Springer Verlag, New York).

The small molecules isolated from these organisms are produced by enzymes encoded within clusters of genes on the chromosomes of these organisms. In many cases the small molecules have a number of functional groups and complex stereochemistries which do not easily lend themselves to being reproduced synthetically. In order to make structural modifications to these molecules, changes in the biosynthetic genes responsible for their production are needed. However, vectors currently available for actinomycetes do not have the versatility of vectors used in *E. coli*, so DNA inserts have to be recloned in other vectors for purposes such as DNA sequencing or synthesis of RNA probes.

Shuttle vectors such as pFD666 (Denis & Brzezinski, *Gene*, 111:115, 1992) have been developed to speed up routine sub-cloning experiments. These vectors should facilitate the cloning, restriction mapping, DNA sequencing, and functional analysis of the actinomycetes genes. However, these vectors require transformation of *E. coli*, purification of the vector from the *E. coli*, and then transformation into actinomycetes. Transformation requires the development of protoplast formation and regeneration protocols each time it is necessary to introduce DNA into a new actinomycetes species, which decreases the simplicity of the process. Additionally, loss of vector and contamination may become factors. Therefore, alternative methods are needed.

An alternative method of performing this genetic manipulation is intergeneric conjugation, which utilizes a system of passing DNA from *E. coli* to actinomycetes directly, i.e., without isolation, purification and manipulation of the DNA by the investigator (Baltz et al., Trends Biotechnol. 1996; 14(7):245-50; Flett et al., FEMS Microbiol. Lett. 1997; 155 (2):223-9; Mazodier et al., J. Bacteriol. 1989; 171(6):3583-5). Intergeneric conjugation has fewer manipulations than transformation, and therefore, the protocol development for each species is quicker. Additionally, the purification of significant quantities of plasmid DNA from *E. coli* is not required for intergeneric conjugation as it is in transformation.

There are a limited number of conjugation vectors that have been prepared to date, and many are derived from SCP2* origin of replication while other vectors have been prepared that comprise a pIJ101 origin of replication. (Keisser et al. Practical *Streptomyces* Genetics, John Innes Centre, Norwich, England, 2000). There is a continuing need in the art to develop bifunctional vectors that may be used to manipulate the biosynthetic genes responsible for small molecule formation.

SUMMARY OF THE INVENTION

The present invention contemplates a vector comprising a nucleic acid encoding a protein operatively associated with an expression control sequence, where the vector contains sequences permitting direct transfer of the vector from a first prokaryotic cell to a second prokaryotic cell. In one embodiment, the vector comprises an *E. coli* origin of replication, an actinomycetes origin of replication, a cos cosmid cloning site, a multiple cloning site, and an origin of transfer. In a further embodiment, the *E. coli* origin of replication is ColE1 and the actinomycetes origin of replication is pJV1. In certain embodiments, the first prokaryotic cell is *E. coli* and the second prokaryotic cell is an actinomycetes. In a specific embodiment, the vector has a vector map as depicted in FIG. 1.

The present invention also contemplates a host cell transfected by the vector as defined above. In one embodiment, the host cell is an *E. coli*.

The present invention further contemplates a method of expressing a protein in a prokaryotic cell, wherein the method comprises the steps of (a) conjugating a first cell comprising the vector described above with a second cell, wherein the vector is transferred from the first cell to the second cell, and the vector comprises a nucleic acid encoding the protein; and (b) expressing the protein in the second cell. In a preferred embodiment, the expressed protein is a protein that is modified. Preferably, at least one amino acid in a protein is replaced or deleted to produce a modified protein. In another embodiment, the nucleic acid is incorporated into the second bacterial cell genome by homologous recombination. In yet another embodiment, the vector has a vector map as depicted in FIG. 1. In a further embodiment, the first bacterial cell is *E. coli* and the second bacterial cell is actinomycetes.

DETAILED DESCRIPTION OF THE INVENTION

Figure 1:
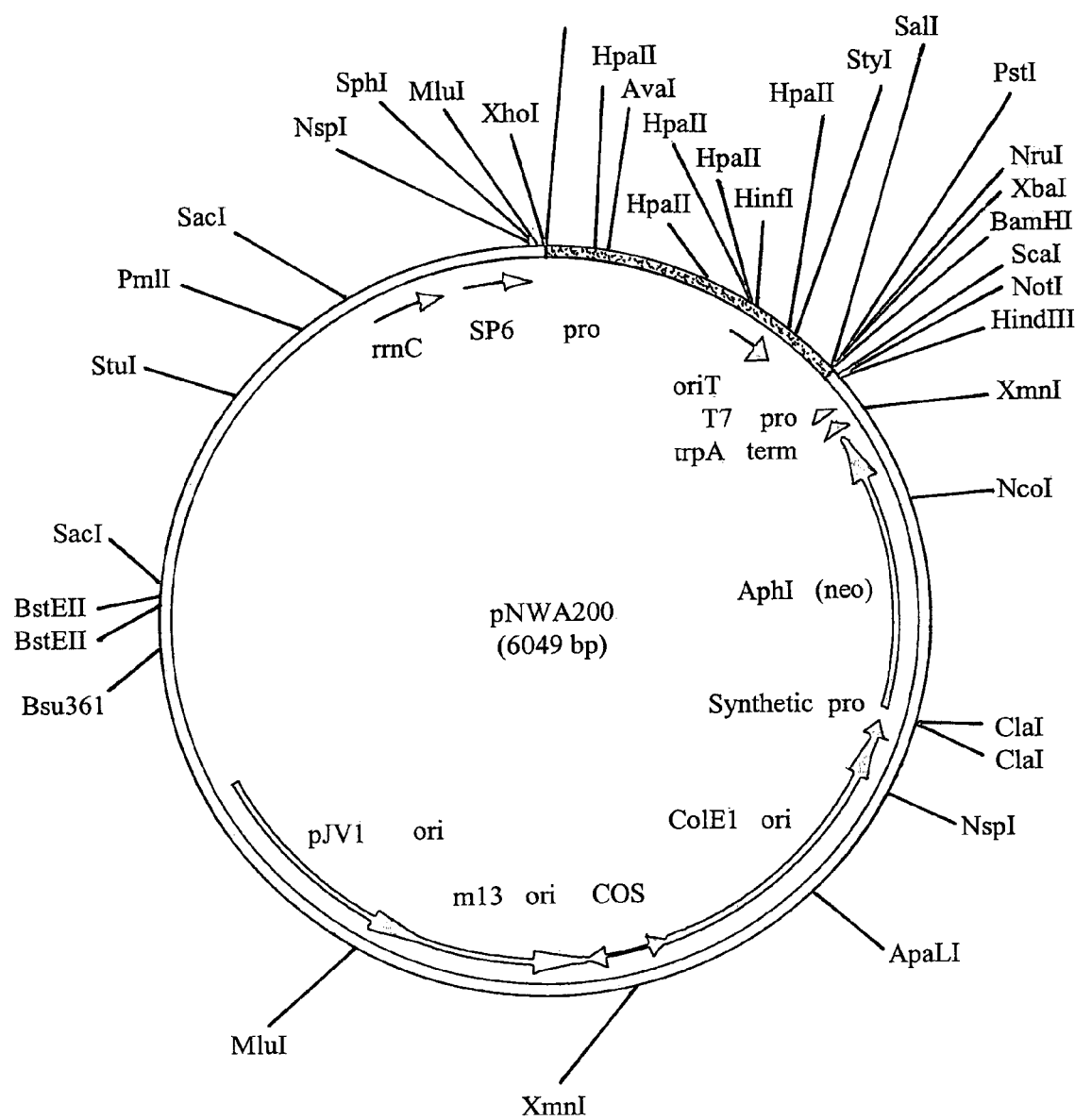
FIG. 1. Diagram of pNWA200.
Figure 2A:
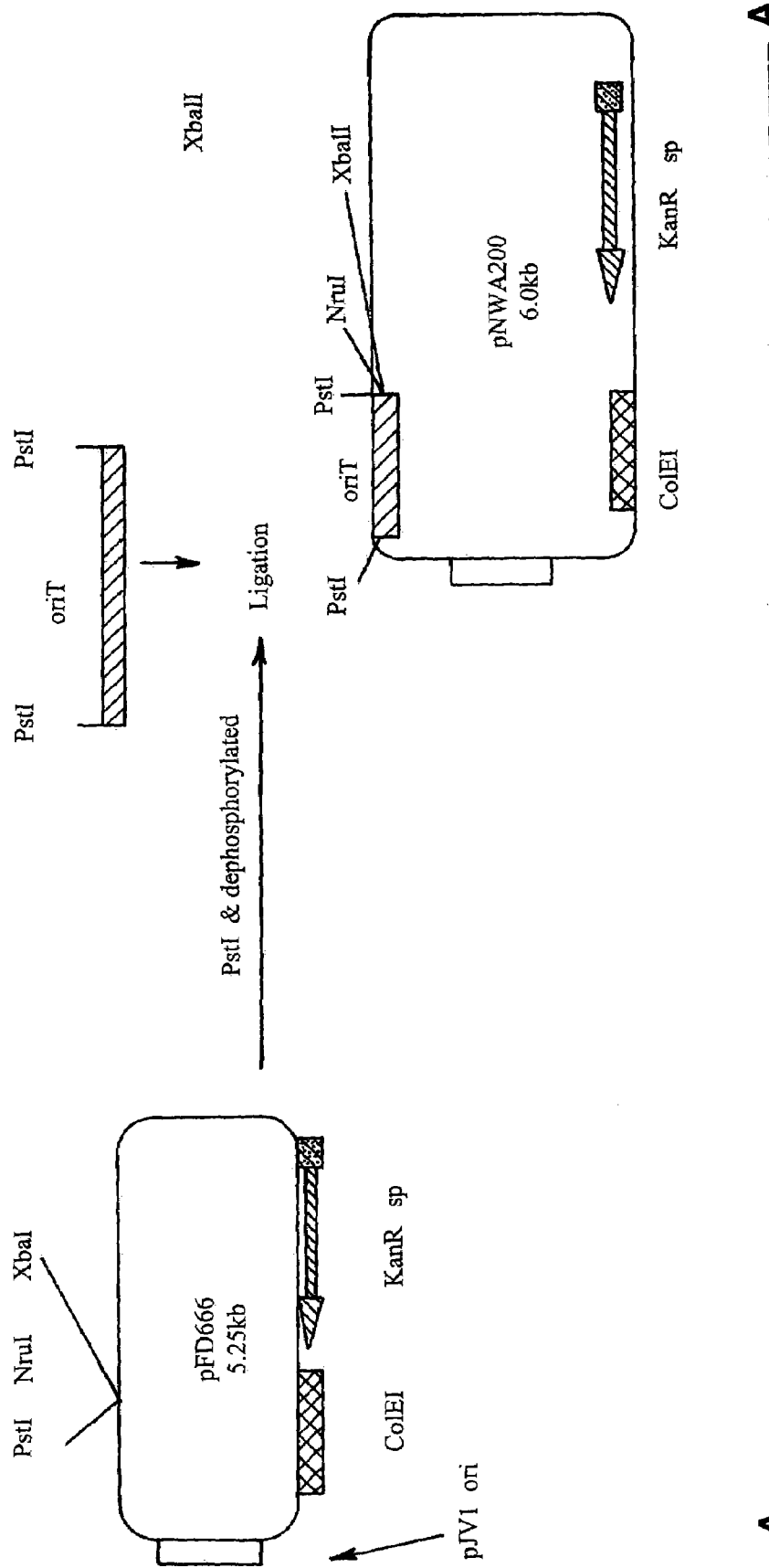
FIGS. 2A-E. Construction scheme of bifunctional/conjugative Peptide Synthetase disruption plasmid: pNWA115.
Figure 2B:
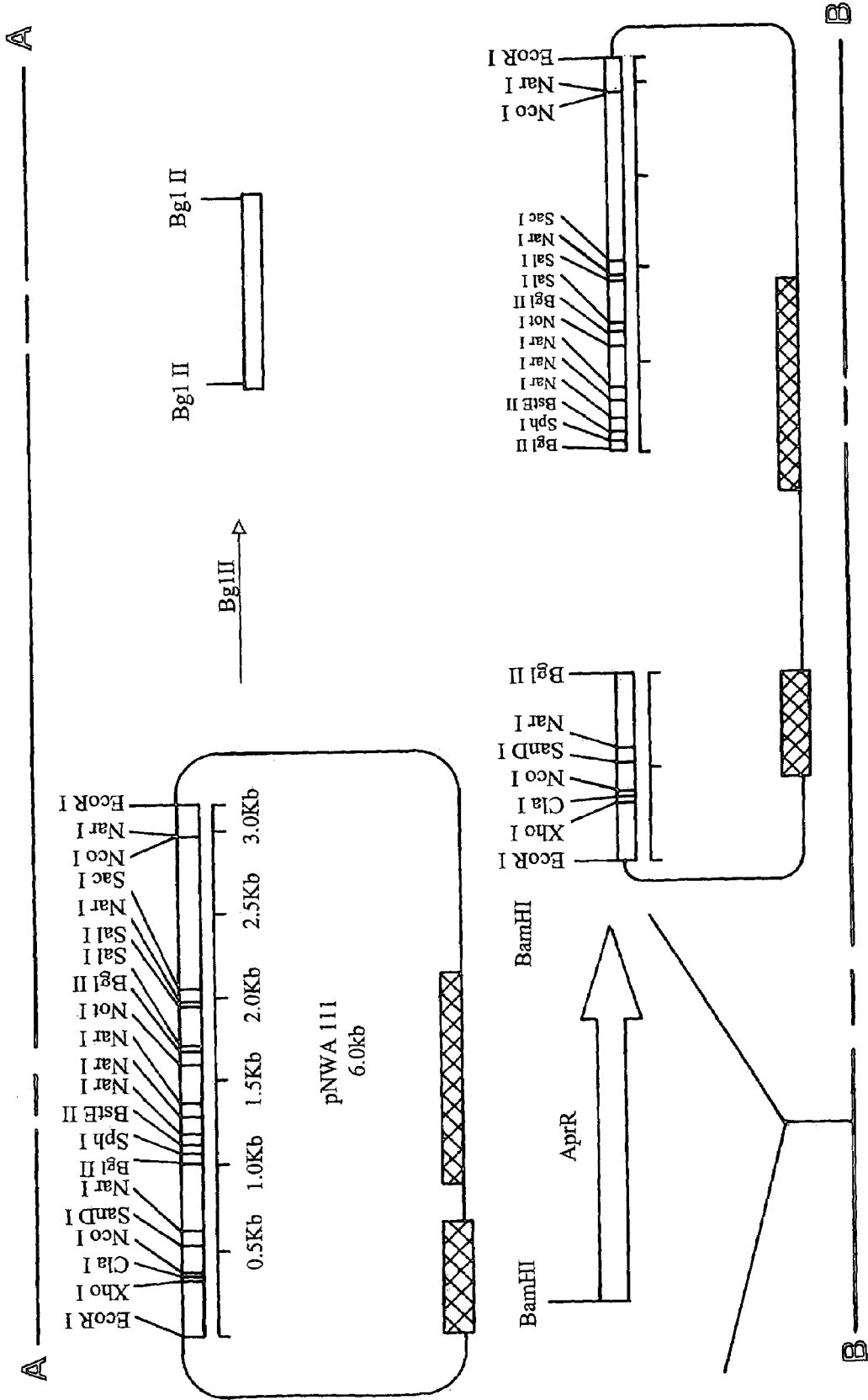
Figure 2C:
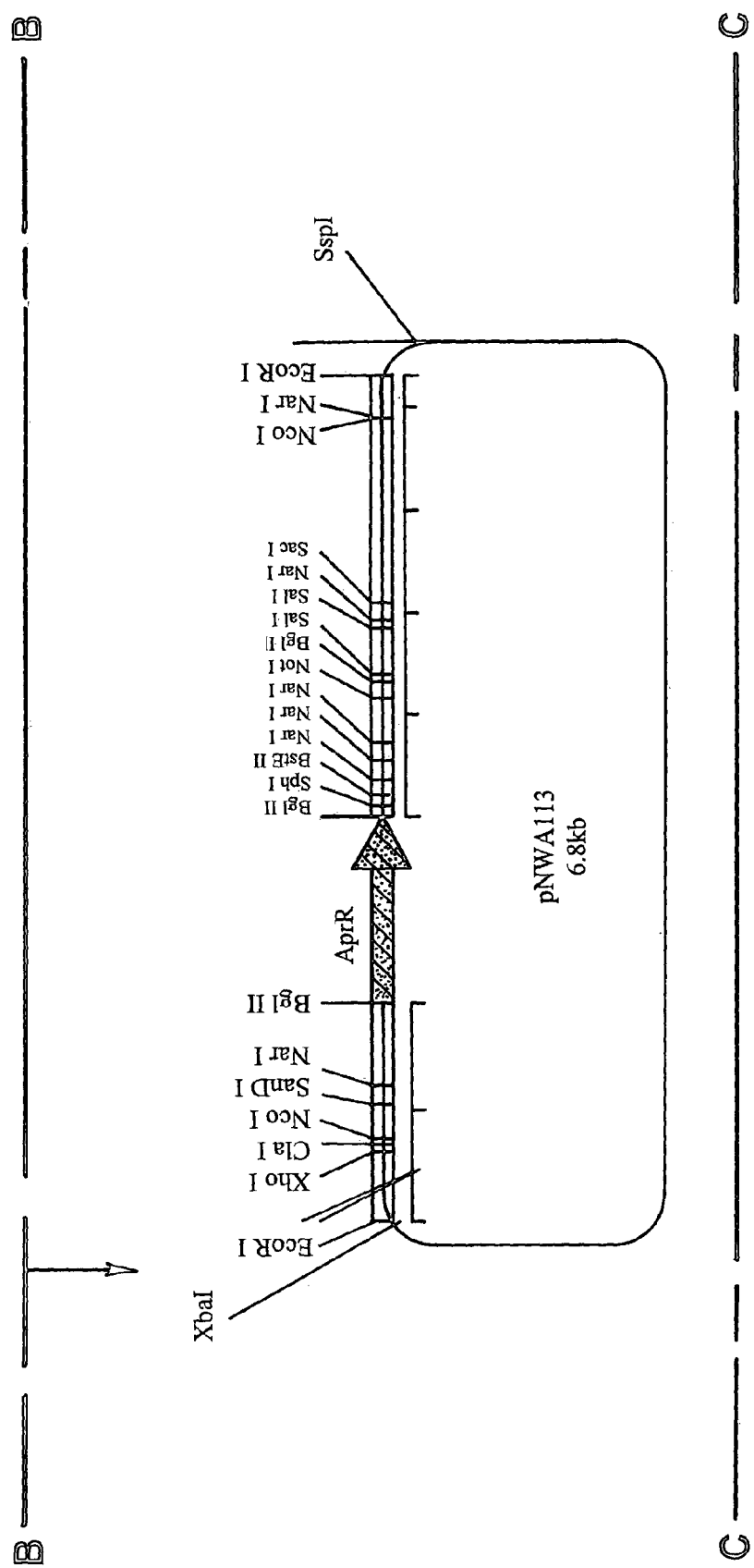
Figure 2D:
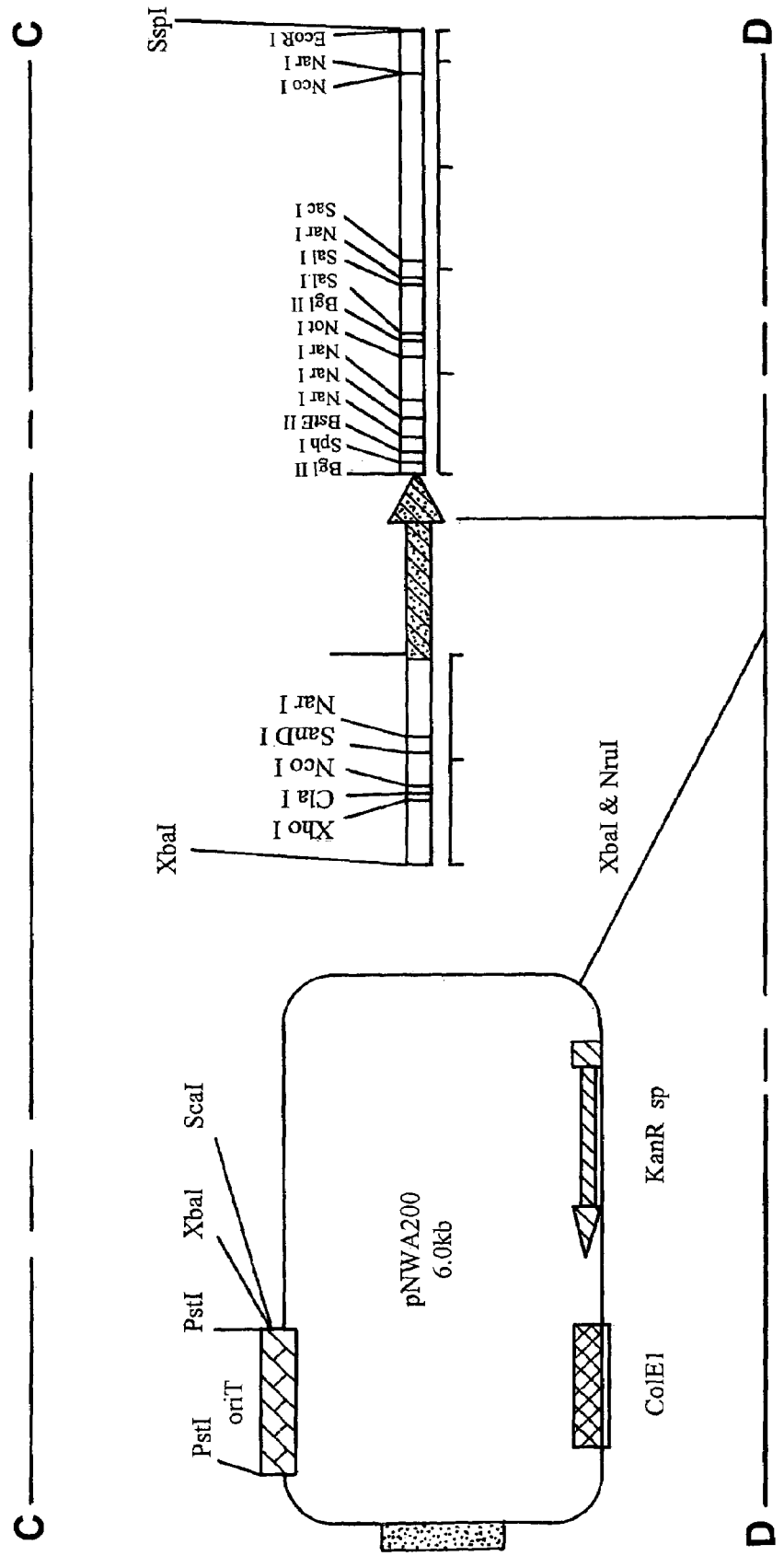
Figure 2E:
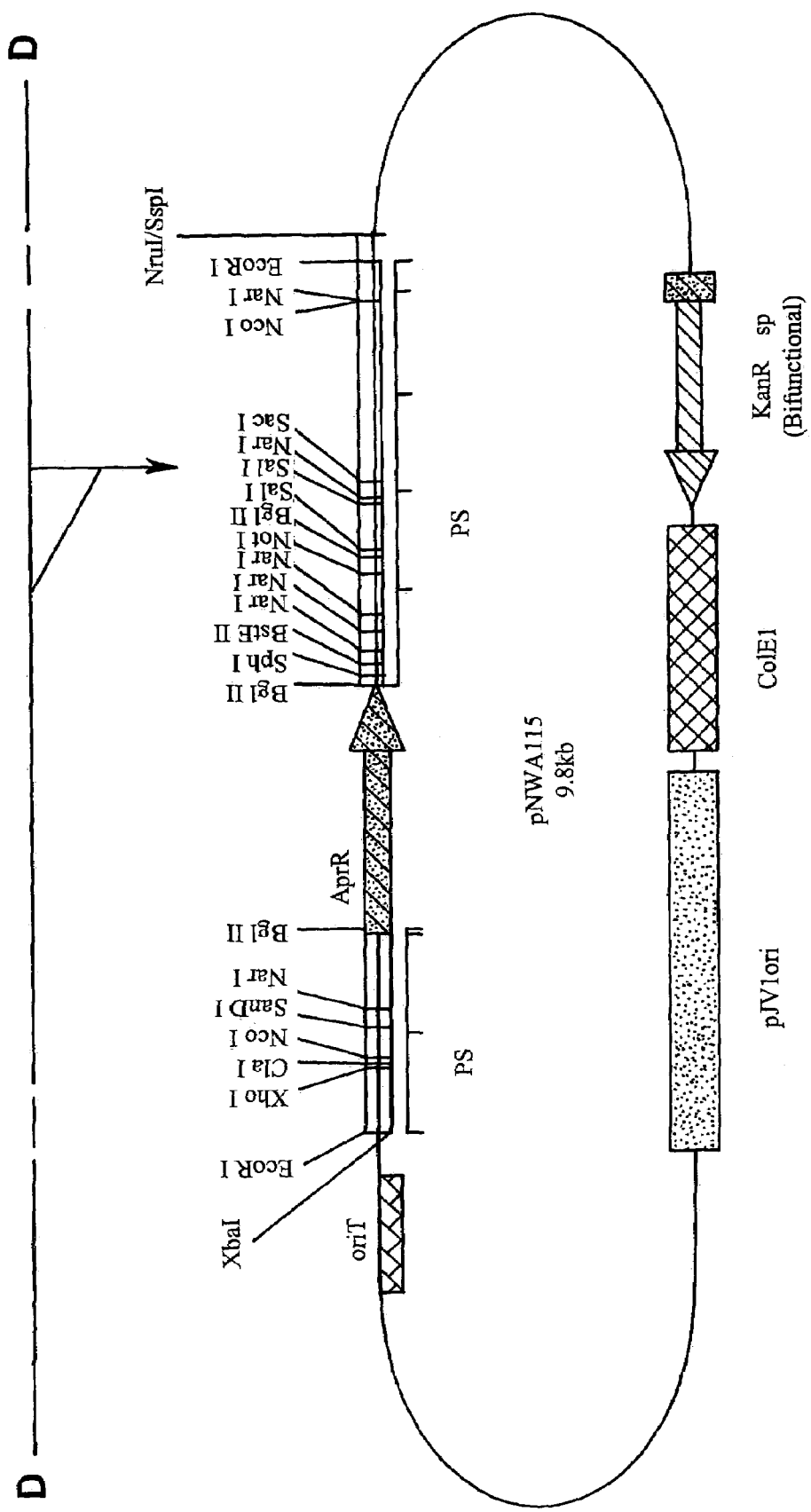

The present invention contemplates a vector that comprises at least one Gram-negative and at least one Gram-positive origin of replication. The origins of replication allow for replication of the nucleic acid encoded by the vector, in either a Gram-negative or a Gram-positive cell line. In one embodiment, the vector comprises one Gram-negative and one Gram-positive origin of replication. Additionally, the vector comprises a multiple cloning site that allows for the insertion of a heterologous nucleic acid that may be replicated and transcribed by a host cell. In a preferred embodiment, the vector comprises an *E. coli* origin of replication and an actinomycetes origin of replication. More preferably, the *E. coli* origin of replication is ColE1 and the actinomycetes origin of replication is pJV1. The sequences of these origins of replication are well known and can be determined by one of ordinary skill in the art. The present vector further comprises an origin of transfer (oriT) which allows for the transfer of the vector from one bacteria to another. Therefore, the present vector system allows for transfer of the vector between two different bacterial strains. The present vector system also has a wide host cell range and may be used in hosts such as, but not limited to, *E. coli, Streptomyces* sp., and *Saccharopolyspora erythraea*.

The most evolved mechanism of transfer of nucleic acids is conjugation. As used herein, the term "conjugation" refers to the direct transfer of nucleic acid from one prokaryotic cell to another via direct contact of cells. The origin of transfer can reside on a vector, so that both donor and recipient cells obtain copies of the vector. Transmissibility by conjugation is controlled by a set of genes in the tra region (present on the host chromosome or on a separate plasmid), which also has the ability to mobilize the transfer of chromosomes when the origin of transfer is integrated into the chromosome (Pansegrau et al., *J. Mol. Biol.*, 239:623-663, 1994; Fong and Stanisich, *J. Bact.*, 175:448-456, 1993). Conjugation has been detected in many species of Gram-positive and Gram-negative bacteria. Such species that are capable of conjugation include, but are not limited to, *Acetobacter xylinum, Achrombacter parvulus, Acinetobacter* spp., *Aeromonas* spp., *Agrobacterium* spp., *Alcaligenes* spp., *Anabaena* spp., *Azospirrillum brazilense, Azotobacter* spp., *Bordetella* spp., *Caulobater* spp., Enterobacteriaceae, *Haemophilus influenzae, Hypomycrobium* X, *Legionella pneumophila, Methylophilus methyltrophus, ethylosinus trichosporium, Myxococcus xanthus, Neisseria* spp., *Paracoccus denitrificans, Pseudomonas* spp., *Rhizobium* spp., *Rhodopseudomonas* spp., *Rhodospirillum* spp., *Thiobacillus* spp., *Vibrio cholerae, Xanthomonas* spp., *Yersinia enterocolitica, Myxococcus*, and *Bacteroides*. Conjugate plasmids may contain the information for producing the sex pilus, which may be required for direct contact of the cells and provides a pathway through which the plasmid passes. The plasmids may allow for a surface exclusion mechanism that reduces conjugal efficiency between bacteria carrying the same plasmid type and may further possess a special system for replication and transfer of plasmid DNA.

A "prokaryotic cell" or "prokaryote" refers to a cell without discrete nucleus and with single, circular DNA molecules within the cytoplasm. Prokaryotes include but are not limited to cells of bacteria and blue green algae.

As used herein, the term "direct transfer" refers to the passing of a nucleic acid sequence from one cell to another without isolation or manipulation of the sequence by the investigator. In a preferred embodiment, the nucleic acid sequence is a vector. In a further embodiment, the direct transfer is a consequence of conjugation of the two cells.

The origin of transfer (oriT) represents the site on the vector where the transfer process is initiated. It is also defined genetically as the region required in cis to the DNA that is to be transferred. Conjugation-specific DNA replication is initiated within the oriT region which also encodes plasmid transfer factors. The oriT nucleic acid sequence may be obtained from any source which harbors an IncPα known in the art such as, but not limited to, *E. coli*. In another embodiment, the nucleic acid sequence is obtained from *E. coli* plasmid RP4 (GenBank Accession No.: X54459). In a more preferred embodiment, the nucleic acid sequence of the oriT is 5'-ccgccagcctcgcagagcaggattcccgttgagcaccgccaggtgcgaataagggacagtgaagaaggaacacccgctcgagggtgggcctacttcacctatcctgaaagg-3' (SEQ ID NO:1; GenBank Accession No.: K00832; Guiney et al., Proc. Natl. Acad. Sci. U.S.A. 1983; 80 (12): 3595-3598).

As discussed above, the vector comprises two separate origins of replications (ori). As used herein, the term "origin of replication" refers to a nucleic acid sequence that initiates nucleic acid replication. At the origin, the two strands of DNA are pulled apart to form a replication bubble. This creates a region of single stranded DNA on each side of the bubble. The DNA polymerase machinery can then move in and begin to synthesize the new strands of DNA, using the old strands as templates. A replication "fork" moves along the DNA in either direction from the origin, synthesizing new DNA. For small DNAs, including bacterial plasmids and small viruses, there is generally a single origin of replication.

In the present invention, one origin of replication allows for plasmid replication in a Gram-negative cell such as, but not limited to, *E. coli*. The second origin of replication allows for plasmid replication in a Gram-positive cell such as, but not limited to, an actinomycete. The origin of replication may be obtained from any known bacterial species. However, the ori may need to be compatible with the host cell in which it will replicate. In a preferred embodiment, the vector comprises an *E. coli* ori (ColE1) and an actinomycetes ori (such as obtained from pJV1).

The nucleotide sequence discussed above (SEQ ID NO. 1) may be incorporated into any vector that may be useful in conjugation. Such vectors may be defined by those of ordinary skill in the art. The vector may be a small, high-copy-number, broad-host range cosmid. Such a vector includes, but is not limited to, pFD666. The vector used may include none or some of the nucleic acid sequence designated SEQ ID NO. 1. Therefore, only the sequences needed may be incorporated into the vector to produce the vector of the present invention. For example, if the vector may include a sequence for an origin of transfer sequence that would be compatible with the prokaryotes that are to be used then an additional origin of transfer may not need to be included into the vector. The sequences may be included into the vector by using conventional molecular biological, microbiological, and recombinant DNA techniques within the skill of the art. Such techniques are discussed below.

A "Campbell recombination event" refers to integration of a vector into genomic DNA by a single, reciprocal, homologous recombination event.

As used herein, the term "modified protein" refers to a protein that has been mutated. The mutation may include, but is not limited to, amino acid insertion, amino acid deletion, or amino acid replacement. The mutation may be produced by any method known in the art.

As used herein "small molecules" include but are not limited to organic or inorganic molecules which are less than about 2 kDa in molecular weight, are more preferably less than about 1 kDa in molecular weight, and/or are able to cross the blood-brain barrier or gain entry into an appropriate cell.

Conjugation may be performed using protocols, methods, and equipment that are known to one of ordinary skill in the art. For example, the methods described in Keiser et al., Practical *Streptomyces* Genetics, John Innes Foundation, John limes Centre, (England), 2000 may be used. Any modifications known in the art may be used.

Molecular Biology

Conventional molecular biology, microbiology, and recombinant DNA techniques within the skill of the art may be employed, in accordance with this invention. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRE Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

"Amplification" of DNA as used herein denotes the use of polymerase chain reaction (PCR) or other methods to increase the concentration of a particular DNA sequence within a mixture of DNA sequences. For a description of PCR see Saiki et al., Science 1988, 239:487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides" in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene", means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

The terms "vector", "cloning vector", and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of specific enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid" which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence that initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign (i.e., extrinsic or extracellular) gene or foreign nucleic acid into a cell. The term "transformation" means the introduction of a foreign gene, foreign nucleic acid, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

The term "expression system" means a host cell and compatible vector under suitable conditions, e.g. for the expression of a protein coded for by foreign DNA carried by the vector and introduced to the host cell. In a specific embodiment, the host cell of the present invention is a Gram-negative or Gram-positive bacteria. These bacteria include, but are not limited to, *E. coli* and *Streptomyces* species. An example of a *Streptomyces* species that may be used includes, but is not limited to, *Streptomyces hygroscopicus*.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, more preferably at least 85%, most preferably at least 90%, and which has the same or substantially similar properties or functions as the native or parent protein or enzyme to which it is compared.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, *Version* 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 5×Denhardt's, and no formamide; or 30% formamide, 5×SSC, 0.5% SDS, 5×Denhardt's). Moderate stringency hybridization conditions correspond to a higher $T_m$, e.g., 40% formamide, with 5× or 6×SCC, 5×Denhardt's. High stringency hybridization conditions correspond to the highest $T_m$, e.g., 50% formamide, 5× or 6×SCC, 5×Denhardt's. SCC is a 0.15M NaCl, 0.015M Na-citrate buffer. 5×Denhardt's is 0.1% ficoll, 0.% g polyvinylpyrrolidone, 0.1% g BSA (w/v). Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, [high stringency] refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Abbreviations are as follows: HPLC refers to high-performance liquid chromatography; SCP2 refers to a 31 kb, circular, low-copy-number plasmid originally identified in *Streptomyces* coelicolor A3; TFA refers to trifluoroacetic acid; GC

Methods of Modifying Bacterial Proteins

The vector of the present invention may be used in a variety of ways to further evaluate the bacterial genome and expressed proteins. In general, the vector may be used to produce specific modifications with a protein sequence to determine the effect of such modification. Non-limiting examples include (i) evaluation of the biological activity of a protein, and (ii) manipulation of a synthetic pathway to alter the final product from bacteria. More detailed discussion of these proposed uses follows.

Knowledge of the primary sequence of the protein, and the similarity of that sequence as compared to proteins of known function, can provide an indication of the function of the protein and the location of the protein within the biosynthetic pathway of a compound.

The present invention contemplates a method for using the vector of the present invention to manipulate or modify a protein to evaluate that proteins function. For example, the vector may be used to alter, delete, or insert amino acids into the protein of interest. Thus, any alterations in activity due to the mutation may be evaluated. The vector, therefore, is used to modify the protein of interest to assess the function of the protein in a biosynthetic pathway. The protein may be any protein of interest including, but not limited to, cytosolic proteins, membrane bound proteins, and proteins integrated within a cellular membrane. In a preferred embodiment, the protein is involved in synthesis of a compound of interest. The prokaryotic cell may be cultured under any conditions that allow for cellular survival and replication. Such conditions are easily determined by one of ordinary skill in the art.

To conjugate the first prokaryotic cell to the second prokaryotic (e.g., bacteria cells) cell, which allows for transfer of the plasmid from one cell to another, the cells may be contacted under conditions that allow for formation of the sex pilus. Such condition determination is well within the level of the art and is discussed supra. Upon conjugation, the cells are maintained so as to allow for transfer of the plasmid from the first cell to the second cell. Conjugation efficiency may vary for different strains and optimal conjugation conditions are usually based upon modifications of the method of Mazodier et al. J. Bacteriol. 1989, 171:3583-3585.

Upon transfer of the plasmid to the second cell, the plasmid may be maintained episomally or the nucleic acid encoding the modified protein of interest may be incorporated into the second cell genome by homologous recombination. As generally defined, "episomal" (and derivatives of the term) refers to a genetic determinant that can replicate autonomously in bacterial cytoplasm. Comparatively, "homologous recombination" involves incorporation of the heterologous nucleic acid into the genome, preferably into the location where the wild-type allele is. In general, homologous recombination involves an endonulcease that introduces single-strand nicks into wild-type allele and the plasmid. The sequences are "exchanged." Since these are homologous chromosomes, the strands can base pair readily with each other. The single strand nicks are sealed by DNA ligase. Preferably, the nucleic acid encoding the modified protein of interest in incorporated into the genome by homologous recombination.

Upon isolation of a prokarytic cell, the host cell can be cultured under conditions that allow for expression of the protein. The transformed cell may be used for a variety of biological assays to assess the effect of the modification. Such assays include, but are not limited to, in vitro biochemical assays, protein isolation and characterization, and analysis of the compound(s) produced by the biosynthetic pathway in which the protein is involved.

Evaluation of the Biological Activity of a Protein

Evaluation of the mechanism of a protein and role the protein plays in the synthesis of a compound has traditionally been determined using sequence homology techniques. However, such techniques may not be accurate and better methods of evaluating novel proteins need to be developed. The vector of the present invention may be used to assess the biological activity of an unknown protein. The vector may be used to disrupt a protein, either by partial or complete removal of the gene encoding the protein or by disruption of the gene encoding the protein. Evaluation of the products produced when the altered protein is present is useful in determining the function of the protein.

Manipulation of a Synthetic Pathway to Alter the Final Product

As discussed above, many compounds obtained from organisms have complex stereochemistries. These compounds are not amenable to production by conventional synthetic methods. Therefore, new methods are needed to produce altered products.

The present invention contemplates a method for using the vector of the present invention to manipulate, modify, or isolate a protein involved in the synthesis of a specific product. For example, the vector of the present invention may be used to alter an enzyme, which is involved in incorporation of an alanine residue into a peptide, so that a tyrosine residue is incorporated instead. The effect of this modification on peptide function may be then be evaluated for biological efficacy. In the above example, modifications to the enzyme may include, but are not limited to, removal of amino acids and/or sequences that specifically recognize alanine and/or incorporation of amino acids and/or sequences that specifically recognize tyrosine.

Therefore, in general terms, the vector of the present invention may be used to alter a gene sequence by insertion of nucleic acid sequences, deletion of nucleic acid sequences, or alteration of specific bases within a nucleic acid sequence to alter the sequence of a protein of interest; thereby producing a modified protein of interest. Preferably, the protein of interest is involved in the synthesis of a compound of interest. The method of modifying a protein comprises (i) transfecting a first prokaryotic cell with the vector of the present invention, (ii) culturing the first prokaryotic cell under conditions that allow for replication of the vector, (iii) conjugating the first prokaryotic cell with a second prokaryotic cell under conditions that allow for the direct transfer of the vector from the first prokaryotic cell to the second prokaryotic cell, and (iv) isolating the second prokaryotic cell transformed with the vector. In a preferred embodiment, the first cell is a Gram-negative bacterial cell and the second cell is a Gram-positive bacterial cell.

EXAMPLES

The present invention will be better understood by reference to the following Examples, which are provided as exemplary of the invention, and not by way of limitation.

Vector pFD666 was deposited on Apr. 19, 2006, in the American Type Culture Collection (ATCC), 10801 University Boulevard, Manassas, Va. 20110-2209, under the provisions of the Budapest Treaty on the International Recognition of the Deposit of Microorganisms for the Purposes of Patent Procedure, and assigned ATCC Patent Deposit Designation No. PTA-7539.

Materials and Methods

Materials

DNA restriction and modification enzymes and T4 DNA ligase were obtained from New England Biolabs. Plasmid DNA was isolated using commercial kits (Qiagen, Valencia, Calif.) and DNA fragments were purified using commercial kits (Tetra Link International). Competent *E. coli* cells were obtained from Stratagene. All were used according to manufacturer's specifications and with buffers and reagents supplied by the manufacturer. *Streptomyces* chromosomal DNA was prepared according to published protocols (Keisser et al. Practical *Streptomyces* Genetics, John Innes Centre, Norwich, England, 2000). Antibiotics were purchased from Sigma.

Example I pNWA200 Vector Preparation

A purified PstI fragment containing oriT from the R plasmid, RP4, was ligated to pFD666 (Denis & Brzezinski, *Gene*, 111:115, 1992), which was then linearized by digestion with PstI and dephosphorylated with calf intestinal phosphatase. This ligation mixture was transformed into competent XL-10 *E. coli* cells (Stratagene, La Jolla, Calif.) following manufacturer's directions. The transformed cells were then plated onto nutrient agar plates containing 50 µg/ml kanamycin and incubated at 37° C. for 1 day. The incubation resulted in about 150 colonies. The colonies were replica plated onto a second kanamycin containing agar plate covered by a positively charged nylon filter, and after 6 hours incubation, the nylon filter containing the embedded colonies was treated with 0.5M NaOH (in 1M NaCl) to lyse the bacteria and denature their DNA according to standard Southern blotting procedures (Southern et al., *J. Mol Biol.*, 98:503, 1975). The nylon filter was probed with a radioactively labeled 0.76 kb PstI fragment and one colony was selected on the basis of its hybridizing signal. The recombinant plasmid was then extracted from a fresh culture of the original hybridizing colony. Digestion of the plasmid with PstI produced two DNA fragments which electrophoresed to positions of 5.25 kb and 0.76 kb, corresponding to linear pFD666 (5.25 kb) and the 0.76 kb oriT containing PstI fragment. This recombinant vector replicated stably in *E. coli* strains and did not show genetic rearrangement upon repeated subculturing and further isolation.

Example II pNWA115 Vector Preparation

A 3.8 kb XbaI/SspI fragment from a *Streptomyces hygroscopicus* strain encoding part of a putative antibiotic biosynthetic gene was cloned into the unique EcoRI site of pUC18 generating the pWA111 plasmid (see FIG. 2). An internal 0.7 kb segment was deleted from the cloned fragment by digestion of pNWA111 with BglII. A 1.5 kb BamHI Fragment containing an apramycin resistant gene (AprR) was isolated from pJV176 and inserted into the BglII site of pNWA111, resulting in pNWA113. Insertion of AprR disrupted the cloned segment of the putative biosynthetic gene. This disrupted fragment was isolated from pNWA113 by digestion with XbaI and SspI and inserted into pNWA260, digested with XbaI and NruI resulting in pNWA115.

ET12567 (MacNeil et al., *Gene*, 111:61, 1992), is a kanamycin-resistant *E. coli* containing pUZ8002 (Xia, et al., Wei Sheng Wu Xue Bao 2002; 42(2):181-5), which is a non-transferable oriT-mobilizing plasmid, carrying the transfer functions and a chlormaphenicol resistant gene, pNWA115 was transferred into ET12567 made competent by calcium chloride treatment following standard protocols (Sambrook, supra). Transformed cells containing pNWA115 were selected by plating the transformation mix on LB agar (Difco) containing apramycin (50 µg/ml), kanamycin (50 µg/ml), and chlormaphenicol (25 µg/ml)

Results pNWA115 was used to determine if pNWA200 is able to replicate and transfer actinomycete DNA from *E. coli* to actinomycete strains via intergeneric conjugation. A recombinant ET12567/pUZ8002 transformant containing pNWA115 was selected on the basis of resistance to kanamycin, chloramphenicol and apramycin. pNWA115 was re-isolated and restriction analysis of the harvested plasmid ensured that no genetic rearrangements had occurred.

Example III

Intergeneric Conjugation

A concentrate of a log-phase culture of the ET12567/pUZ8002 transformant containing pNWA115, grown in LB broth supplemented with the described antibiotics, was prepared. This culture was mixed with spore preparations of two representative actinomycetes; *Streptomyces lividans* 1326 and *Streptomyces hygroscopicus*. Spores were harvested and titered to approximately $10^8$ CFU/ml. Conditions employed were similar to those previously described for intergeneric conjugation (Flett et al, *FEMS Microbiol Lett*, 155:223, 1997). From the mating approximately $10^{-1}$ exconjugants/recipient were obtained from the conjugation plate containing the *Streptomyces lividans* 1326, and approximately $10^{-2}$ exconjugants/recipient were obtained from conjugation plates for *Streptomyces hygroscopicus*. Recombinant *Streptomyces hygroscopicus* strains were screened for sensitivity to kanamycin and resistance to apramycin after successive replica plates onto plates containing apramycin selection only. Kanamycin sensitivity indicated that pNWA115 was not being maintained in the strain as an autonomously replicating plasmid while apramycin resistance indicated that the manipulated high % GC cloned DNA fragment had integrated into the chromosome.

The resulting recombinant mutants of *Streptomyces hygroscopicus* were then grown in liquid culture, and genomic DNA was extracted. The genomic DNA was digested with a number of restriction endonucleases (KpnI, XhoI, NcoI, XbaI, and PstI). The digested DNA was subjected to Southern hybridization under standard conditions (Sambrook, supra) using the cloned 3 kb EcoRI fragment labeled with $^{32}$P as the probe. Hybridization patterns were compared to similar digests of genomic DNA isolated from the parental *Streptomyces hygroscopicus* strain.

To check for antibiotic production, samples were removed from 50 ml cultures of a representative isolate carrying the disrupted gene grown at 28° C. in Tryptone Soya Broth medium (Oxoid, Ogdensburg, N.Y.) and were analyzed by HPLC. 20 µl aliquots were loaded onto a Waters 4 mm×50 mm YMC ods-a-column and eluted with a gradient of 10% acetonitrile/90% TFA (20%) in water to 34% acetonitrile/66% TFA in water over 15 minutes. Chromatograms were compared to chromatograms of samples taken from a similarly treated culture of the parental strain.

Results

Figure 3A:
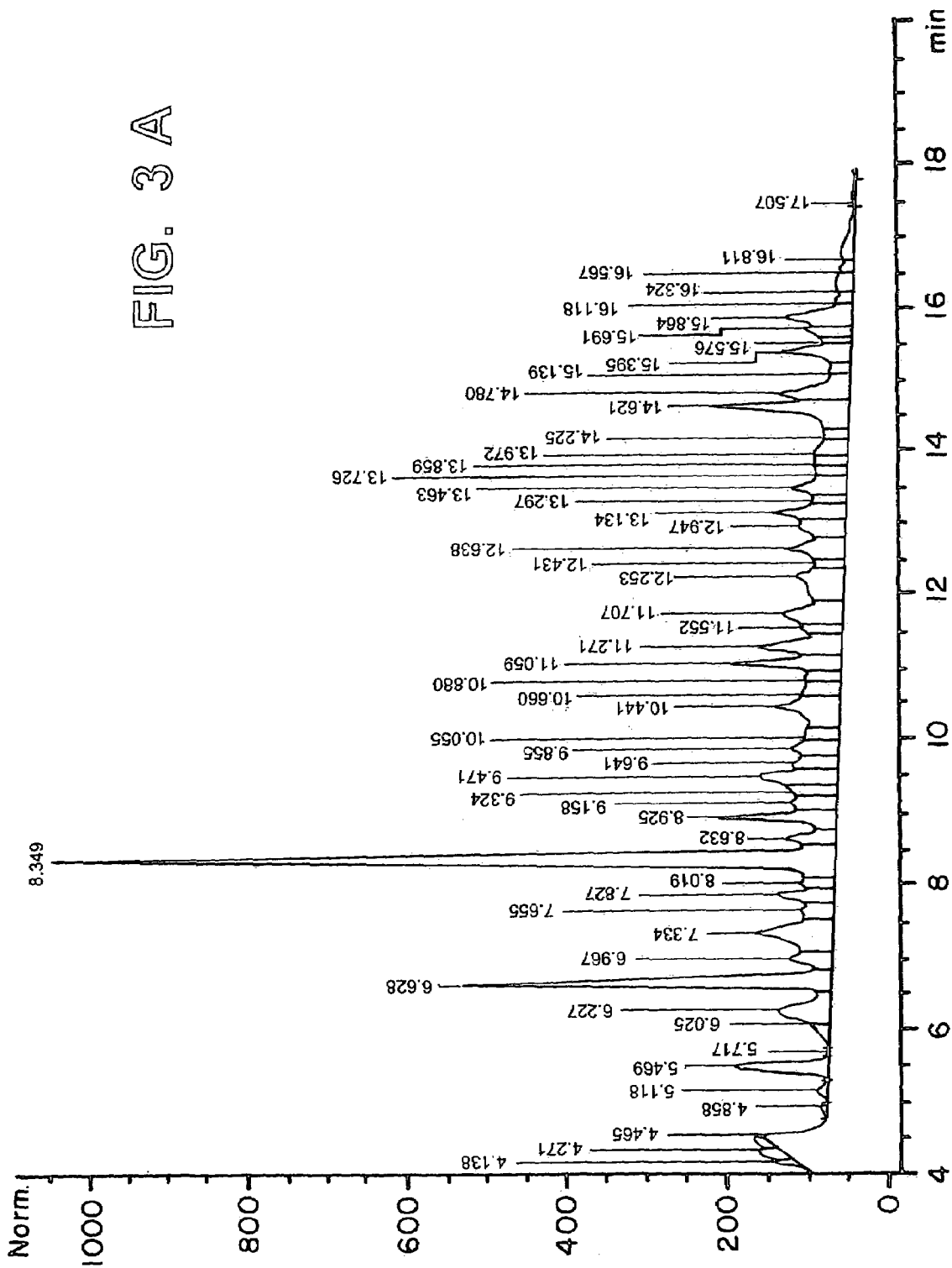
FIGS. 3A-B. Representative chromatograms of cells transformed (3B) or not transformed (3A) with pNWA115.
Figure 3B:
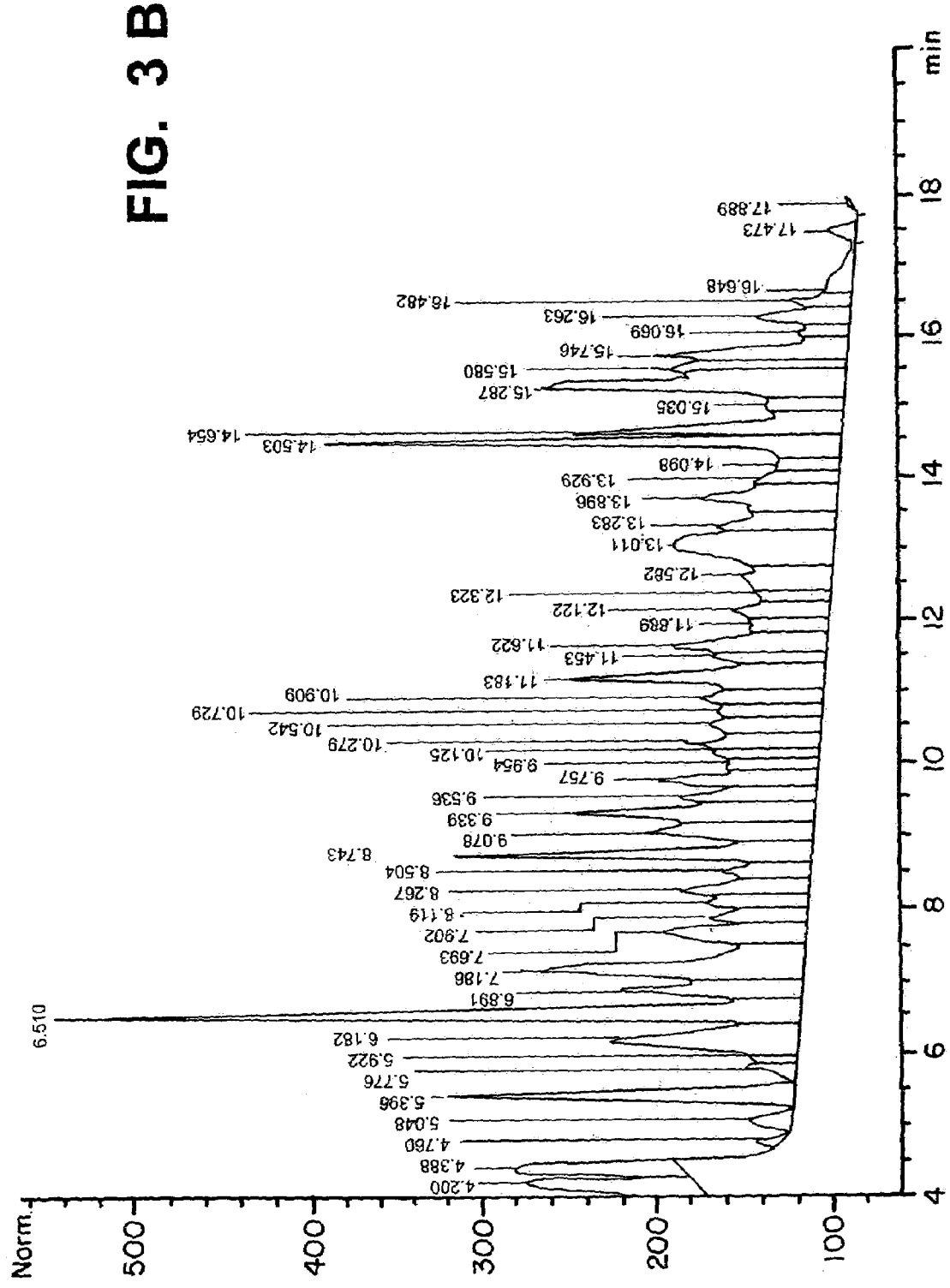

The Southern hybridization results showed that the apramycin resistance gene had integrated into the genome by homologous recombination between the putative antibiotic biosynthetic gene cloned in pNWA115 and the wild type allele in the host chromosome. A double cross-over recombination event resulted in replacement of the wild type allele with the cloned, disrupted DNA fragment. Changes in the size of the restriction fragments hybridizing to the 3 kb EcoRI fragment was consistent with insertion of the apramycin resistant gene into the region of the chromosome homologous to the putative antibiotic biosynthetic coding region. Fermentation of this recombinant *Streptomyces* strain demonstrated that the mutant strains no longer produced the antibiotic, as expected. FIG. 3A is an example of a chromatogram resulting from HPLC analysis of the fermentation broth of the parental strain. Antibiotic production is indicated by the material eluting at 8.348, 11.059, and 13.134 minutes, previously identified as various forms of the antibiotic. FIG. 3B is an example of a chromatogram resulting from HPLC analysis of the fermentation broth of a disruption mutant. It can be seen that the antibiotic associated peaks are absent, demonstrating that the cloned DNA in pNWA115 is part of an antibiotic biosynthesis gene cluster.

CONCLUSIONS pNWA200 is a unique vector that is effective for cloning and manipulating high % GC DNA in *E. coli* and has the ability to efficiently transfer such modified DNA to actinomycetes through intergeneric conjugation. In addition, this vector can be used to identify, modify, or inactivate actinomycete genes involved in the production of novel and potentially useful secondary metabolites.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

What is claimed is:

1. An intergeneric shuttle vector comprising an expression control sequence; a multiple cloning site into which a nucleic acid encoding a polypeptide can be inserted that is positioned such that when the nucleic acid is inserted into the multiple cloning site the nucleic acid is operatively associated with the expression control sequence; an *E. coli* origin of replication; an actinomycetes origin of replication from pJV1; a cos cosmid cloning site; and an origin of transfer (OriT) that directs transfer of the vector from an *E. coli* cell to an actinomycetes cell during conjugation, and wherein the shuttle vector has a vector map according to pNWA200.

2. A host cell comprising the vector of claim 1.

3. The host cell of claim 2, wherein the host cell is an *E. coli* cell.

4. The intergeneric shuffle vector of claim 1 further comprising said nucleic acid encoding a polypeptide inserted into said multiple cloning site such that said nucleic acid is operatively associated with said expression control sequence.

5. An intergeneric shuttle vector comprising an expression control sequence; a multiple cloning site into which a nucleic acid encoding a polypeptide can be inserted that is positioned such that when the nucleic acid is inserted into the multiple cloning site said nucleic acid is operatively associated with the expression control sequence; an *E. coli* origin of replication; an actinomycetes origin of replication from pJV1; a cos cosmid cloning site; and an origin of transfer (OriT) that directs transfer of the shuttle vector from an *E. coli* cell to an actinomycetes cell during conjugation, and wherein the shuttle vector has a vector map according to pNWA115.

6. A host cell comprising the vector of claim 5.

7. The host cell of claim 6, wherein the host cell is an *E. coli* cell.

8. The intergeneric shuttle vector of claim 5 further comprising said nucleic acid encoding a polypeptide inserted into said multiple cloning site such that said nucleic acid is operatively associated with said expression control sequence.

9. A method of expressing a polypeptide comprising (i) culturing an *E. coli* cell comprising the shuttle vector of claim 4 with an actinomycetes cell; (ii) allowing direct transfer of the vector from said *E. coli* cell to said actinomycetes cell to occur via conjugation; and (iii) expressing the polypeptide in said actinomycetes cell.

---

SEQUENCE LISTING

```
<160> NUMBER OF SEQ ID NOS: 1

<210> SEQ ID NO 1
<211> LENGTH: 112
<212> TYPE: DNA
<213> ORGANISM: Plasmid RK2
<300> PUBLICATION INFORMATION:
<308> DATABASE ACCESSION NUMBER: GenBank / K00832
<309> DATABASE ENTRY DATE: 1993-04-26
<313> RELEVANT RESIDUES: (1)..(112)

<400> SEQUENCE: 1
ccggccagcc tcgcagagca ggattcccgt tgagcaccgc caggtgcgaa taagggacag      60
tgaagaagga acacccgctc gagggtgggc ctacttcacc tatcctgaaa gg            112
```

10. The method according to claim 9, wherein the nucleic acid encoding a polypeptide comprises a modified nucleotide sequence and the expressed polypeptide is a modified polypeptide.

11. The method according to claim 10, wherein the modification comprises insertion of a heterologous nucleotide sequence, deletion of a nucleotide sequence, or alteration of a least one nucleotide within the sequence.

12. The method according to claim 9, further comprising in step ii, identifying a recipient cell wherein the nucleic acid encoding the polypeptide is incorporated into the genome of said recipient cell by homologous recombination and wherein said step (iii) of expressing the polypeptide comprises expressing the polypeptide in said recipient cell.

13. The method according to claim 9, wherein the actinomycetes cell is *Acetobacter xylinum, Achrombacter parvulus, Acinetobacter* spp., *Aeromonas* spp., *Agrobacterium* spp., *Alcaligenes* spp., *Anabaena* spp., *Azospirrillum brazilense, Azotobacter* spp., *Bordetella* spp., *Caulobater* spp., Enterobacteriaceae, *Haemophilus influenzae, Hypomycrobium* X, *Legionella pneumophila, Methylophilus methyltrophus, Ethylosinus trichosporium, Myxococcus xanthus, Neisseria* spp., *Paracoccus denitrificans, Pseudomonas* spp., *Rhizobium* spp., *Rhodopseudomonas* spp., *Rhodospirillum* spp., *Thiobacillus* spp., *Vibrio cholerae, Xanthomonas* spp., *Yersinia enterocolitica, Myxococcus* or *Bacteroides*.

14. A method of expressing a polypeptide comprising:
  (i) culturing an *E. coli* cell comprising the shuttle vector of claim 8 with an actinomycetes cell;
  (ii) allowing direct transfer of the vector from said *E. coli* cell to said actinomycetes cell to occur via conjugation; and
  (iii) expressing the polypeptide in said actinomycetes cell.

15. The method according to claim 14, wherein the nucleic acid encoding a polypeptide comprises a modified nucleotide sequence, and whereby the expressed polypeptide is a modified polypeptide.

16. The method according to claim 15, wherein the modification comprises insertion of a heterologous nucleotide sequence, deletion of a nucleotide sequence, or alteration of a least one nucleotide within the sequence.

17. The method according to claim 14, further comprising in step ii, identifying a recipient cell wherein the nucleic acid encoding the polypeptide is incorporated into the genome of said recipient cell by homologous recombination and wherein said step (iii) of expressing the polypeptide comprises expressing the polypeptide in said recipient cell.

18. The method according to claim 14, wherein said actinomycetes cell is *Acetobacter xylinum, Achrombacter parvulus, Acinetobacter* spp., *Aeromonas* spp., *Agrobacterium* spp., *Alcaligenes* spp., *Anabaena* spp., *Azospirrillum brazilense, Azotobacter* spp., *Bordetella* spp., *Caulobater* spp., Enterobacteriaceae, *Haemophilus influenzae, Hypomycrobium* X, *Legionella pneumophila, Methylophilus methyltrophus, Ethylosinus trichosporium, Myxococcus xanthus, Neisseria* spp., *Paracoccus denitrificans, Pseudomonas* spp., *Rhizobium* spp., *Rhodopseudomonas* spp., *Rhodospirillum* spp., *Thiobacillus* spp., *Vibrio cholerae, Xanthomonas* spp., *Yersinia*.

* * * * *